United States Patent [19]

Hoelderich et al.

[11] Patent Number: 4,939,280

[45] Date of Patent: Jul. 3, 1990

[54] CONVERSION OF 1,3-DIOXANES TO 4-OXAALDEHYDES

[75] Inventors: Wolfgang Hoelderich; Franz Merger, both of Frankenthal; Helmut Lermer, Mannheim, all of Fed. Rep. of Germany

[73] Assignee: BASF Aktiengesellschaft, Ludwigshafen, Fed. Rep. of Germany

[21] Appl. No.: 188,416

[22] Filed: Apr. 29, 1988

[30] Foreign Application Priority Data

May 12, 1987 [DE] Fed. Rep. of Germany ....... 3715752

[51] Int. Cl.$^5$ ................. C07D 213/48; C07D 307/46; C07D 333/22
[52] U.S. Cl. ..................................... 549/13; 568/443; 568/450; 546/268; 546/283; 546/284; 549/59; 549/60; 549/78; 549/473; 549/502
[58] Field of Search ..................... 568/427, 443, 450; 549/78, 13, 59, 60, 473, 502; 546/268, 283, 284

[56] References Cited

U.S. PATENT DOCUMENTS

| | | | |
|---|---|---|---|
| 3,676,500 | 7/1972 | Mantell | 568/427 |
| 3,965,208 | 6/1976 | Butter et al. | 585/454 |
| 4,691,063 | 9/1987 | Engel et al. | 568/783 |
| 4,709,097 | 11/1987 | Hoelderich et al. | 549/498 |

FOREIGN PATENT DOCUMENTS 02922698 11/1980 Fed. Rep. of Germany.
3513725 10/1986 Fed. Rep. of Germany ...... 568/450

OTHER PUBLICATIONS

J. Am. Chem. Soc. 892 (1960) 6419.
J. Am. Chem. Soc. 84 (1962) 3307.
European Search Report.

Primary Examiner—Joseph Paul Brust
Assistant Examiner—M. S. Howard
Attorney, Agent, or Firm—Keil & Weinkauf

[57] ABSTRACT

4-Oxaaldehydes of the formula

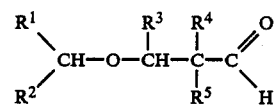

are prepared by catalytic isomerization of 1,3-dioxanes by a process in which a 1,3-dioxane of the formula

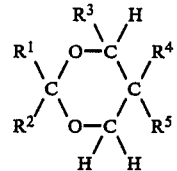

where $R^1$, $R^2$, $R^4$ and $R^5$ are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl or alkenylaryl radical of 5 to 16 carbon atoms or a heterocyclic radical, and furthermore $R^1$ and $R^2$ and/or $R^4$ and $R^5$ together with the carbon atom to which they are bonded may form a cycloalkane, a cycloalkene or a heterocyclic structure, and the stated radicals may furthermore carry substituents which are inert under the reaction conditions, and $R^3$ is hydrogen or straight-chain or branched alkyl, is isomerized using a phosphate as a catalyst.

4 Claims, No Drawings

CONVERSION OF 1,3-DIOXANES TO 4-OXAALDEHYDES

The present invention relates to a process for the preparation of 4-oxaaldehydes by catalytic isomerization of 1,3-dioxanes.

It is known that 1,3-dioxane and its derivatives can be subjected to a rearrangement reaction to give 8-alkoxyaldehydes (J. Am. Chem. Soc. 892 (1960), 6419 and J. Am. Chem. Soc. 84 (1962), 3307). Silica gel and pumice are used as catalysts. The catalysts used show pronounced signs of deactivation. Furthermore, their activity and selectivity are unsatisfactory. Because of the lack of specificity of the natural product pumice, which has different compositions depending on its origin, uncontrollable effects on the reaction cannot be avoided (Houben-Weyl, Methoden d. org. Chemie IV, 2, page 149 (1955)).

German Laid-Open Application No. DOS 2,922,698 describes a process for the preparation of β-alkoxypivalaldehyde from 1,3-dioxanes using silica, doped with hydroxides of group III A and/or III B and alkali metal hydroxide, as a catalyst. These catalysts, which constitute only a slight advance in the art differ from those described above by virtue of the neutralization of the acid centers. The compounds of the pure lanthanides praseodymium and neodymium, which are required for producing the catalyst, are expensive and are not readily available chemicals. The preferably used commercial lanthanide mixture didymium varies in its composition, so that the industrial catalysts are difficult to reproduce. The reported catalyst lives are only of the order of hours; nothing is said about the regeneration of the catalysts.

It is an object of the present invention to provide a process for the preparation of 4-oxaaldehydes from the corresponding 1,3-dioxanes in the presence of catalysts which are readily available, have a high activity and are easily regenerated. Furthermore, long catalyst lives in combination with high conversions and selectivities should be ensured.

We have found that this object is achieved by a process for the preparation of 4-oxaaldehydes of the formula (I)

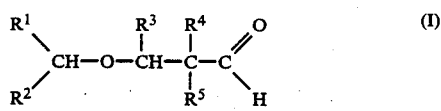

(I)

by catalytic isomerization of 1,3-dioxanes, wherein a 1,3-dioxane of the formula (II)

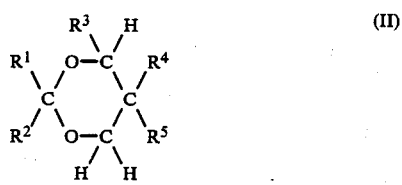

(II)

where $R^1$, $R^2$, $R^4$ and $R^5$ in the formulae (I) and (II) are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl, aralkenyl or alkenylaryl radical of 6 to 16 carbon atoms or a heterocyclic radical and moreover $R^1$ and $R^2$ and/or $R^4$ and $R^5$ together with the carbon atom to which they are bonded may form a cycloalkane, cycloalkene or a heterocyclic structure containing 5 to 7 ring members, and the stated radicals may furthermore carry substituents which are inert under the reaction conditions and $R^3$ is hydrogen or a straight-chain or branched alkyl radical, is isomerized using a phosphate as a catalyst.

In the novel process, the catalyst requirements set out at the beginning are substantially fulfilled. In view of the prior art, the result obtained in the process is particularly surprising as this prior art points exactly in the opposite direction, i.e. indicates the exclusion of the acid centers. It was therefore not to be expected that precisely with acidic phosphates, which are distinguished by particularly high acidity and, in the case of the phosphates having a zeolite structure, by stringent structural parameters, excellent results would be obtained within wide limits.

The conversion of 1,3-dioxanes to 4-oxaaldehydes is a good method for preparing, for example, the ethers of the hydroxyneoalkanals in high selectivity and high conversion, the said ethers being impossible or difficult to obtain by conventional etherification methods.

The conversion can be represented by the following equation:

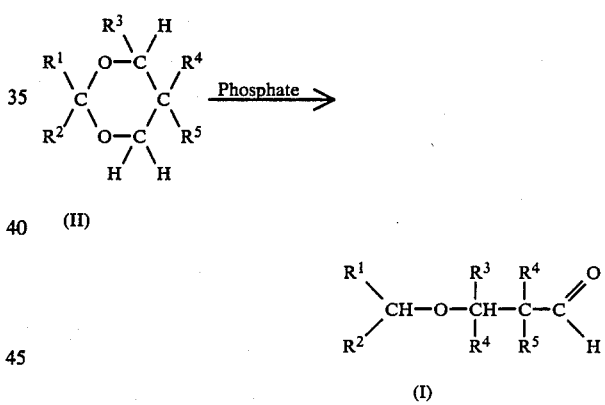

The 1,3-dioxanes of the formula (II) which are used as starting materials, and accordingly the resulting 4-oxaaldehydes of the formula (I), contain the radicals $R^1$, $R^2$, $R^4$ and $R^5$, which are identical or different and independently of one another are each hydrogen, a straight-chain or branched alkyl, alkenyl or alkynyl radical of not more than 18, in particular from 1 to 12, preferably from 1 to 6, carbon atoms, a cycloalkyl or cycloalkenyl radical of 5 to 8, in particular 5 or 6, carbon atoms, an aryl, alkylaryl, aralkenyl or alkenylaryl radical of 6 to 16, in particular 6 to 12, carbon atoms, or an aromatic saturated or unsaturated heterocyclic structure which contains one or more heteroatoms, such as nitrogen, oxygen or sulfur. The stated radicals may furthermore carry substituents which are inert under the reaction conditions.

The products (I) formed from compound (II) can in turn be reacted with a diol and thus convert, via an acetal of the general formula (IV)

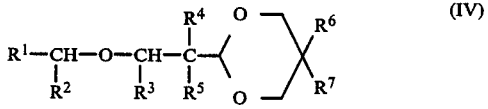

where $R^6$ and $R^7$ have the abovementioned meanings of $R^4$ and $R^5$, to an aldehyde of the structure

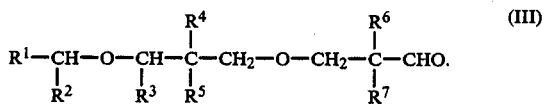

$R^1$ and $R^2$ and/or $R^4$ and $R^5$ and/or $R^6$ and $R^7$ together with the carbon atom to which they are bonded may furthermore form a cycloalkane, a cycloalkene or a heterocyclic structure. Suitable radicals $R^3$, independently of the other radicals, are hydrogen and straight-chain or branched alkyl of 1 to 12, in particular 1 to 8, preferably 1 to 4, carbon atoms.

Alkyl, alkenyl or alkynyl is, for example, methyl, ethyl, n-propyl, isopropyl, propenyl, isopropenyl, n-butyl, isobutyl, n-butenyl, isobutenyl, pentyl, pentenyl, pentynyl, hexyl, hexenyl, heptyl, heptenyl, octyl, octenyl, nonyl, nonenyl, decyl, decenyl, dodecyl or dodecenyl. The alkyl, alkenyl or alkynyl radicals may furthermore carry substituents which are inert under the reaction conditions, e.g. halogen, alkoxy or carboxyl.

Cycloalkyl is, for example, cyclopentyl, cyclohexyl, cycloheptyl, cyclopentenyl or cyclohexenyl.

Suitable aromatic radicals are, for example, phenyl, benzyl, 2-phenylethyl, 3-phenylpropyl, 2-phenylpropyl, 4-phenylbutyl, 3-phenylbutyl, 2-phenylbutyl and 3-phenylbutenyl, and these radicals may furthermore be substituted by radicals which are inert under the reaction conditions.

Heterocyclic and heteroaromatic radicals are, for example, tetrahydrofuran, dihydrofuran, furan, tetrahydrothiophene(thiophane), dihydrothiophene, thiophene, pyridine and thiopyran radicals. These radicals may furthermore be substituted by radicals which are inert under the reaction conditions, such as alkyl or halogen.

Starting materials which are particularly suitable for the novel process are 1,3-dioxanes in which $R^3$ is hydrogen and $R^4$ and $R^5$ are each one of the stated organic radicals.

The starting compounds of the formula (II) can be prepared by a conventional method from aldehydes or ketones or their readily cleavable derivatives, for example dialkyl ketals or acetals, and 1,3-diols, in accordance with the following equation:

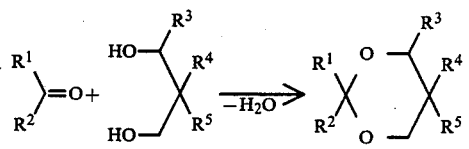

Examples of suitable diol components are the following compounds: propane-1,3-diol, 2-methyl-, 2-ethyl-, 2-phenyl-, 2,2-dimethyl-, 2,2-diethyl-, 2-methyl-2-ethyl-, 2-methyl-2-propyl-, 2-methyl-2-butyl-, 2-methyl-2-phenyl- and 2-ethyl-2-butylpropane-1,3-diol, 1,1-dimethylolcyclohexane and -pentane, 3,3-dimethyloltetrahydrofuran and -pyran and 2,2,4-trimethylpentane-1,3-diol.

Examples of suitable carbonyl components are aliphatic, aromatic or heterocyclic aldehydes and ketones or their acetals or ketals with low-boiling alcohols.

Examples of saturated aliphatic aldehydes are formaldehyde, acetaldehyde, propionaldehyde, butyraldehyde, pentanal, hexanal and higher homologous n-alkanals, such as decanal, isobutyraldehyde, 2-methylbutanal, 3-methylbutanal, 3,3-dimethylbutanal, 2-methylpentanal, 2-ethylhexanal and 2-methyldecanal, glyoxal, methylglyoxal, malondialdehyde, succindialdehyde and glutardialdehyde.

Examples of heterocyclic aldehydes are tetrahydrofuran-2-aldehyde and -3-aldehyde, tetrahydrothienyl-2- and -3-aldehyde, 5,6-dihydropyran-6-aldehyde, 2,5-dimethyl-5,6-dihydropyran-6-aldehyde, furan-2-aldehyde and -3-aldehyde, thienyl-3-aldehyde and pyridine-2-, -3- and -4-aldehyde.

Examples of suitable ketones are the following compounds: acetone, methyl ethyl ketone, diethyl ketone, methyl isopropyl ketone, diisopropyl ketone, diisobutyl ketone, methyl isobutyl ketone, methoxyacetone, methyl vinyl ketone, methyl isopropenyl ketone, methyl isobutenyl ketone, cyclopentanone, cyclohexanone, methylcyclopentanones, methylcyclohexanones, cyclohexenone, 3,5,5-trimethylcyclohexen-2-one, methyl, ethyl and vinyl phenyl ketone, methyl furyl ketone, acetyl acetone and ethyl acetoacetate.

Examples of other substituted alkanals are 3-hydroxy-2,2-dimethylpropanal, methoxy- and butoxypivalaldehyde, 4-acetoxybutyraldehyde and ethyl 5-formylvalerate.

It is also possible to use unsaturated aldehydes, e.g. acrolein, α-methylacrolein, α-ethylacrolein and higher α-alkyl-, isoalkyl- and alkenylacroleins, such as but-2-enal, 2-methyl-but-2-enal, 2-methylpent-2-enal, 2-ethylhex-2-enal, 2,2-dimethylpent-4-enal, 2-methyl-4-acetoxybut-2-enal, 2-methoxymethylacrolein, 2-(3-methoxycarbonylpropyl)-acrolein or 2-methyl-4-chlorobut-2-enal.

Examples of aromatic aldehydes are benzaldehyde, p-methoxybenzaldehyde, phenylacetaldehyde, 2-phenyl- and 3-phenylpropanal, 2-hydroxybenzaldehyde, 3-hydroxy-4-methoxybenzaldehyde, cinnamaldehyde and benzylacrolein.

Catalysts used for the novel conversion of 1,3-dioxanes are phosphates, aluminum phosphates, silicon aluminum phosphates, silicon iron aluminum phosphates, cerium phosphate, zirconium phosphates, boron phosphates, iron phosphates, strontium phosphates or mixtures of these being particularly suitable.

Aluminum phosphate catalysts advantageously used for the novel process are aluminum phosphates synthesized under hydrothermal conditions. These aluminum phosphates have a zeolite structure.

The aluminum phosphates prepared under hydrothermal conditions are, for example, APO-5, APO-9, APO-11, APO-12, APO-14, APO-21, APO-25, APO-31 and APO-33.

$AlPO_4$-5 (APO-5) can be synthesized, for example, by homogeneously mixing orthophosphoric acid with pseudoboehmite in water; tetrapropylammonium hydroxide is added to this mixture, and the reaction is then carried out at about 150° C. for from 20 to 60 hours under autogenous pressure in an autoclave. The $AlPO_4$ filtered off is dried at from 100° to 160° C. and calcined at from 450° to 550° C.

AlPO4-9 (APO-9) is likewise synthesized from orthophosphoric acid and pseudoboehmite, but in aqueous DABCO solution (1,4-diazabicyclo[2.2.2]octane) at about 200° C. under autogenous pressure in the course of from 200 to 400 hours.

AlPO4-21 (APO-21) is synthesized from orthophosphoric acid and pseudoboehmite in aqueous pyrrolidine solution at from 150° to 200° C. under autogenous pressure in the course of from 50 to 200 hours.

Examples of silicon aluminum phosphates used for the novel process are SAPO-5, SAPO-11, SAPO-31 and SAPO-34. These silicon aluminum phosphates have a zeolite structure and are prepared by crystallization from an aqueous mixture at from 100° to 250° C. and under autogenous pressure in the course of from 2 hours to 2 weeks, the reaction mixture of a silicon, an aluminum, and a phosphorus component in aqueous solutions containing an organic amine being reacted.

Thus, SAPO-5 is obtained, for example, by mixing SiO2, suspended in aqueous tetrapropylammonium hydroxide solution, with an aqueous suspension of pseudoboehmite and orthophosphoric acid, followed by reaction at from 150° to 200° C. in the course of from 20 to 200 hours under autogenous pressure in a stirred autoclave. The powder filtered off is dried at from 110° to 168° C. and calcined at from 450° to 550° C.

Other examples of suitable silicon aluminum phosphates are ZYT-5, ZYT-6, ZYT-7, ZYT-9, ZYT-11 and ZYT-12.

Other suitable phosphate catalysts in the process are precipitated aluminum phosphates. For example, an aluminum phosphate of this type is obtained by dissolving 92 g of diammonium hydrogen phosphate in 700 ml of water and adding a solution of 268 g of Al(NO3)3.H2O in 780 ml of water dropwise to this solution in the course of 2 hours. During this procedure, the pH is kept at 8 by the simultaneous addition of 25% strength NH3 solution. The resulting precipitate is stirred for a further 12 hours and then filtered off under suction, washed thoroughly and dried at 60° C. for 16 hours.

Boron phosphates as catalysts for the novel process can be prepared, for example, by mixing and kneading concentrated boric acid and phosphoric acid followed by drying and calcination in an inert gas, air or steam atmosphere at 258° to 650° C., preferably from 300° to 500° C.

If, when the phosphate catalysts are used according to the invention, deactivation due to coking occurs, it is advisable to regenerate the phosphate catalysts by burning off the coke deposit with air or with an air/N2 mixture at from 300° to 550° C.

By precoking, it is possible to adjust the activity of the catalyst to obtain optimum selectivity of the desired reaction product.

In order to obtain high selectivity, high conversion and long catalyst lives, it is advantageous to modify the phosphate catalysts. In a suitable method of modifying the catalysts, for example, the unmolded or molded phosphate is doped with metal salts by ion exchange or by impregnation. The metals used are alkali metals, such as Li, Cs or K, alkaline earth metals such as Mg, Ca or Sr, metals of main groups 3, 4 and 5, such as Al, Ga, Ge, Sn, Pb or Ni, transition metals of subgroups 4-8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, and rare earth metals, such as La, Ce, Pr, Nd, Er, Yb and U.

The catalysts described here can be used alternatively as 2-4 mm extrudates, as tablets having a diameter of from 3 to 5 mm or as powders having a particle size of from 0.1 to 0.5 mm or in the form of a fluidizable catalyst.

The reaction conditions generally selected for the novel conversion are, in the gas phase, from 200° to 500° C., preferably from 230° to 400° C., and a WHSV of from 0.1 to 20 $h^{-1}$, preferably from 0.5 to 5 $h^{-1}$ (g of 1,3-dioxane per g of catalyst per hour). The reaction can be carried out in a fixed bed or fluidized bed. The reaction may also be effected in the liquid phase by the suspension, tricklebed or liquid phase procedure, at from 50° to 200° C. In general, the conversion increases sharply with increasing temperature, while the selectivity decreases only slightly within a certain temperature range.

The process is carried out as a rule under atmospheric pressure or, depending on the volatility of the starting compound, under reduced or superatmospheric pressure, preferably by a continuous procedure.

Sparingly volatile or solid starting materials can be used in dissolved form, for example in solution in tetrahydrofuran, toluene or petroleum ether. The starting materials may furthermore be diluted with solvents of this type or with inert gases, such as $N_2$, Ar or steam.

After the reaction, the resulting 4-oxaaldehydes are isolated by a conventional method, for example by distillation from the reaction mixture; unconverted 1,3dioxanes are, if desired, recycled to the reaction.

The compounds obtainable by the novel process and a number of their derivatives are of interest as biologically active compounds, for example as bactericides, and are also useful intermediates. They can be readily converted to amines, alcohols and acids by a conventional method, for example by oxidation with oxygen or by reduction, for example, by catalytic hydrogenation or hydrogenation under aminating conditions. The compound of the formula

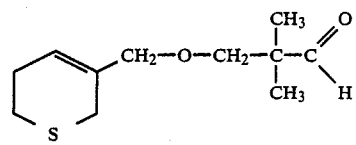

a novel compound of melting point 53.8° C. and boiling point 121°-125° C.

The Examples which follow illustrate the invention. Comparative Example 7 shows that the catalyst described n German Laid-Open Application DOS 2,922,698 is effective for only a short reaction time of from 1 to 2 hours, the activity decreasing virtually to zero after 4 hours.

EXAMPLES 1 TO 18

The reactions are carried out under isothermal conditions in a tubular reactor (coil, 0.6 cm diameter, 90 cm length) in the gas phase in the course of not less than 6 hours. Separation and characterization of the reaction products are carried out by conventional methods. Quantitative determination of the reaction products (I) and of the starting materials (II) was effected by gas chromatography.

The catalysts used in the Examples for the conversion of 1,3-dioxanes to 4-oxaaldehydes are:

Catalyst A

AlPO₄-5 (APO-5) is synthesized by dissolving 200 g of 98% strength phosphoric acid, and suspending 136 g of boehmite, in 335 g of water, adding 678 g of a 30% strength aqueous tetrapropylammonium hydroxide solution and reacting this mixture in a stirred autoclave at 150° C. in the course of 43 hours under autogenous pressure. The crystalline material is filtered off under suction and then dried at 120° C. and calcined at 500° C. for 16 hours. The AlPO₄-5 synthesized in this manner contains 45.5% by weight of Al₂O₃ and 46.5% by weight of P₂O₅. This material is molded with pseudoboehmite in a weight ratio of 60:40 to give 2 mm extrudates, which are dried repeatedly at 120° C. and calcined at 500° C. for 16 hours.

Catalyst B

AlPO₄-21 (APO-21) is synthesized by stirring 200 g of 98% strength phosphoric acid, 156 g of precipitated aluminum hydroxide and 71 g of pyrrolidine together in 900 g of water and then carrying out the reaction at 200° C. under autogenous pressure in the course of 91 hours. The product dried at 120° C. and calcined at 500° contains 56.6% by weight of P₂O₅ and 43.4% by weight of Al₂O₃. This AlPO₄-21 is molded with extrusion assistants to give 2 mm extrudates, which are dried at 110° C. and calcined at 500° C. for 16 hours.

Catalyst C

AlPO₄-9 (APO-9) is synthesized by dissolving 200 g of 98% strength phosphoric acid, and suspending 136 g of boehmite in 400 g of water, adding an aqueous solution of 112 g of diazobicyclo[2.2.2]octane (DABCO) and 320 g of H₂O, and reacting this mixture in a stirred autoclave at 200° C. in the course of 336 hours under autogenous pressure. The crystalline material is filtered off and then dried at 120° C. and calcined at 500° C. for 16 hours. The AlPO₄-9 synthesized in this manner contains 49.0% by weight of P₂O₅ and 37.1% by weight of Al₂O₃. This material is molded with extrusion assistance to give 3 mm extrudates, which are dried repeatedly at 120° C. and calcined at 500° C. for 6 hours.

Catalyst D

SAPO-5 is prepared from a mixture of 200 g of 98% strength phosphoric acid, 136 g of boehmite, 60 g of 30% strength silica sol, 287 g of tripropylamine and 587 g of H₂O. This mixture is reacted at 150° C. in the course of 168 hours under autogenous pressure. After filtration, the crystalline product is dried at 120° C. and calcined at 500° C. SAPO-5 contains 49.8% by weight of P₂O₅, 33.0% by weight of Al₂O₃ and 6.2% by weight of SiO₂. SAPO-5 is molded with an extrusion assistant to give 3 mm extrudates, which are dried at 120° C. and calcined at 500° C.

Catalyst E

Commercially available zirconium phosphate, Zr₃(PO₄)₄ in pure form is molded.

Catalyst F

Catalyst F is a precipitated aluminum phosphate, which is obtained by precipitation from Al(NO₃)₃/H₃PO₄ solution with NH₃ at pH 6–7. The precipitate is filtered off and then dried at 110° C. and calcined at 500° C. The catalyst F contains 28.5% by weight of Al and 13.2% by weight of P.

Catalyst G (Comparison catalyst according to German Laid-Open Application No. DOS 2,922,698)

51 g of a commercial SiO₂ having the specification stated in German Laid-Open Application No. DOS 2,922,698 (D11-11 ®) is impregnated with a solution of 51 g of 0.1 N CH₃COOH, 3.19 g of Pr(NO₃)₃·5 H₂O, 3.21 g of Nd(NO₃)₃·5 H₂O and 2.66 g of CH₃COOK, dried and calcined at 600° C. for 4 hours.

The experimental results obtained with these catalysts are listed in the Tables below.

TABLE 1

$$CH_3CH_2CH_2-\begin{pmatrix} O \\ O \end{pmatrix} \longrightarrow CH_3CH_2CH_2O-CH_2-\underset{\underset{CH_3}{|}}{\overset{\overset{CH_3}{|}}{C}}-C\overset{\nearrow O}{\underset{\searrow H}{}}$$

(II)          (I)

| Example | 1 | 2 | 3 | 4 | 5 | 6 | 7[1] |
|---|---|---|---|---|---|---|---|
| Catalyst | A | B | D | E | E | F | G |
| Temperature [°C.] | 275 | 300 | 300 | 275 | 300 | 275 | 275 |
| WHSV [h⁻¹] | 2 | 3 | 3 | 2 | 2 | 2 | 2 |
| Conversion [%] (II) | 48.9 | 49.6 | 62.7 | 67.5 | 83.4 | 84.1 | 23.0 |
| Selectivity [%] (I) | 72.2 | 66.7 | 80.5 | 82.7 | 76.9 | 53.7 | 11.5 |

[1] Comparative Example $$R-\begin{pmatrix} O \\ O \end{pmatrix} \qquad R-CH_2-O-CH_2-\underset{\underset{CH_3}{|}}{\overset{\overset{CH_3}{|}}{C}}-C\overset{\nearrow O}{\underset{\searrow H}{}}$$

(II)          (I)

| Example | 8 | 9 | 10 | 11 | 12 | 13 | 14 |
|---|---|---|---|---|---|---|---|
| R | $\begin{smallmatrix}CH_3\\ \diagdown\\ CH-\\ \diagup\\ CH_3\end{smallmatrix}$ | | | $CH_3{=}CH{-}CH_2{-}\underset{\underset{CH_3}{\|}}{\overset{\overset{CH_3}{\|}}{C}}-$ | | ⌬ | $\begin{smallmatrix}CH_3\\ \|\\ CH-\end{smallmatrix}$ |
| Catalyst | D | E | F | D | E | D | E |

TABLE 1-continued

| | | | | | | | |
|---|---|---|---|---|---|---|---|
| Temperature [°C.] | 275 | 300 | 275 | 275 | 300 | 275 | 300 |
| WHSV [h$^{-1}$] | 2 | 2 | 2 | 2 | 2 | 2 | 2 |
| Conversion [%] (II) | 44.9 | 70.3 | 45.9 | 22.6 | 35.6 | 62.1 | 73.2 |
| Selectivity [%] (I) | 89.8 | 80.5 | 73.4 | 80.1 | 77.5 | 68.4 | 80.2 |

| Example | 15[(2)] | 16[(2)] | 17[(3)] | 18[(3)] |
|---|---|---|---|---|
| R | 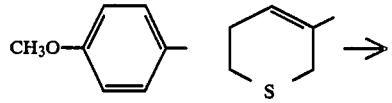 | 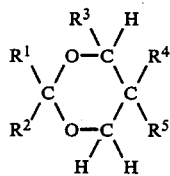 | | |
| Catalyst | E | C | D | F |
| Temperature [°C.] | 275 | 300 | 275 | 275 |
| WHSV [h$^{-1}$] | 2 | 2 | 3 | 2 |
| Conversion [%] (II) | 85.9 | 51.1 | 23.9 | 48.6 |
| Selectivity [%] (I) | 51.9 | 71.6 | 77.8 | 68.2 |

[(2)] Educt diluted with tetrahydrofuran in a weight ratio of 25:75
[(3)] Educt diluted with tetrahydrofuran in a weight ratio of 50:50

We claim:

1. A process for the preparation of a 4-oxaaldehyde of the formula (I)

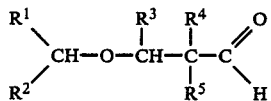

by catalytic isomerization of a 1,3-dioxane, wherein a 1,3-dioxane of the formula (II) Hoelderich et al., Ser. No. 188,416

(II)

where $R^1$, $R^2$, $R^4$ and $R^5$ in the formulae (I) and (II) are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl, aralkenyl or alkenylaryl radical of 5 to 16 carbon atoms or a heterocyclic radical selected from the group consisting of tetrahydrofuran, dihydrofuran, furan, tetrahydrothiophene, dihydrothiophene, thiophene, pyridine and thiopyran and moreover $R_1$ and $R^2$ and/or $R^4$ and $R^5$ together with the carbon atom to which they are bonded may be form a cycloalkane, cycloalkene or a heterocyclic radical, selected from the group consisting of tetrahydrofuran, dihydrofuran, furan, tetrahydrothiophene, dihydrothiophene, thiophene, pyridine and thiopyran and the stated radicals may furthermore carry one or more substituents which are inert under the reaction conditions selected from the group consisting of alkyl and halogen and $R^3$ is hydrogen or a straight-chain or branched alkyl radical,, is isomerized using a catalyst selected from the group consisting of aluminum phosphates having a zeolite structure and precipitated aluminum phosphates.

2. A process as claimed in claim 1, wherein a acetal or ketal of propane-1,3-diol, 2-methyl-, 2,2-dimethyl-, 2-methyl- 2-ethyl-, 2-methyl-2-propyl-, 2-methyl-2-butyl-, 2-methyl-2-phenyl- or 1-isopropyl-2,2-dimethyl-propane-1,3-diol or of 1,1-dimethylolcyclohexane or -pentane is isomerized.

3. A process as claimed in claim 1, wherein the catalyst used is a phosphate having a zeolite structure.

4. A process as claimed in claim 1, wherein the isomerization is carried out in the gas phase.

* * * * *

UNITED STATES PATENT AND TRADEMARK OFFICE
CERTIFICATE OF CORRECTION

PATENT NO. : 4,939,280
DATED : July 3, 1990
INVENTOR(S) : Wolfgang HOELDERICH et al.

It is certified that error appears in the above-identified patent and that said Letters Patent is hereby corrected as shown below:

Claim 1, Lines 5-6, (Column 9, lines 30-31)

Delete "Hoelderich et al., Ser. No. 188,416"

Claim 1, Line 19, (Column 10, line 25)

After "may" delete "be"

Claim 2, Line 1, (Column 10, line 37)

"a" should read --an--

Signed and Sealed this

Thirteenth Day of August, 1991

Attest:

HARRY F. MANBECK, JR.

*Attesting Officer*     *Commissioner of Patents and Trademarks*